United States Patent
Sumiyoshi

(10) Patent No.: US 9,983,180 B2
(45) Date of Patent: May 29, 2018

(54) MASS SPECTROMETRY METHOD, CHROMATOGRAPH MASS SPECTROMETER, AND PROGRAM FOR MASS SPECTROMETRY

(71) Applicant: SHIMADZU CORPORATION, Kyoto-shi, Kyoto (JP)

(72) Inventor: Takashi Sumiyoshi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days. days.

(21) Appl. No.: 15/548,261

(22) PCT Filed: Feb. 4, 2015

(86) PCT No.: PCT/JP2015/053113
§ 371 (c)(1),
(2) Date: Aug. 2, 2017

(87) PCT Pub. No.: WO2016/125271
PCT Pub. Date: Aug. 11, 2016

(65) Prior Publication Data
US 2018/0031529 A1    Feb. 1, 2018

(51) Int. Cl.
G01N 30/72 (2006.01)
H01J 49/26 (2006.01)
G01N 27/64 (2006.01)

(52) U.S. Cl.
CPC ......... *G01N 30/7233* (2013.01); *G01N 27/64* (2013.01); *H01J 49/26* (2013.01)

(58) Field of Classification Search
USPC ............................................... 250/281, 282
See application file for complete search history.

(56) References Cited

U.S. PATENT DOCUMENTS

| 8,653,448 B1 * | 2/2014 | Ueda | H01J 49/00 |
| | | | 250/282 |
| 2008/0128607 A1 * | 6/2008 | Herold | G01N 30/72 |
| | | | 250/282 |

(Continued)

FOREIGN PATENT DOCUMENTS

| JP | 2012-104389 A | 5/2012 |
| JP | 2013-15485 A | 1/2013 |

OTHER PUBLICATIONS

Written Opinion dated Apr. 7, 2015 in application No. PCT/JP2015/053113.

*Primary Examiner* — Kiet T Nguyen
(74) *Attorney, Agent, or Firm* — Sughrue Mion, PLLC

(57) ABSTRACT

A mass spectrometry method includes: creating a plurality of measurement conditions corresponding to all combinations of precursor-ion candidates generated from the target compound and collision-energy-value candidates; performing a product-ion scan measurement using each of the plurality of measurement conditions and performing a plurality of reference measurements for detecting a predetermined kind of ion generated from the target compound under the same condition, within an introduction time during which the target compound is introduced; creating a peak function, which is a function representing a change in the amount of introduction of the target compound into the mass spectrometer within the introduction time, based on the result of the reference measurement; creating a normalization function for normalizing the amount of introduction of the target compound within the introduction time, based on the peak function; and normalizing the intensity of product-ion spectra obtained by the product-ion scan measurements performed for all combinations.

10 Claims, 4 Drawing Sheets

(56) References Cited

U.S. PATENT DOCUMENTS

| | | | | |
|---|---|---|---|---|
| 2010/0099196 A1* | 4/2010 | Mischak | ............ | G01N 33/6887 436/86 |
| 2011/0282587 A1* | 11/2011 | Jones | .................. | H01J 49/0009 702/19 |
| 2017/0154169 A1* | 6/2017 | Paschke | ............. | G01N 30/7266 |

* cited by examiner

Fig. 3A
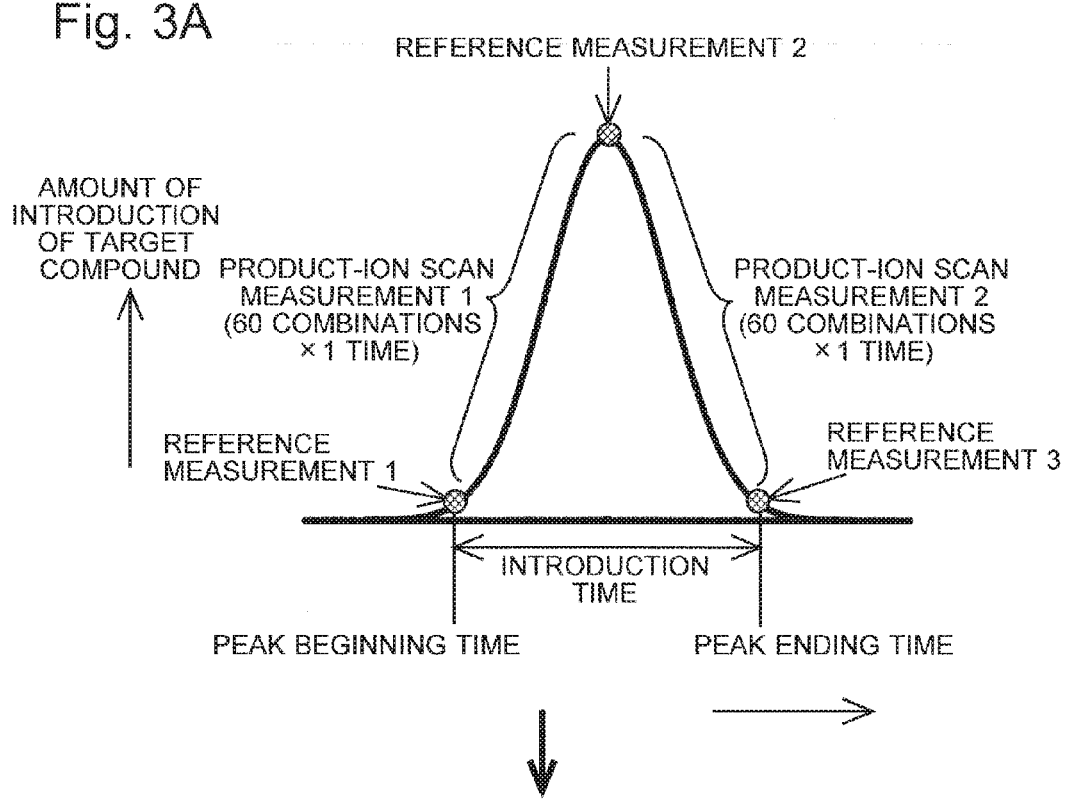
CREATE PEAK FUNCTION
CREATE NORMALIZAITON FUNCTION
Fig. 3B
NORMALIZE INTENSITY OF PRODUCT-ION SPECTRUM OF EACH COMBINATION
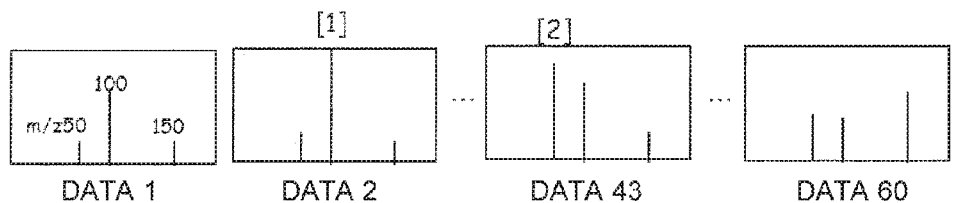
Fig. 3C
MRM MEASUREMENT CONDITION 1:
　PRECURSOR ION 1 (m/z 200) > PRODUCT ION (m/z 100), CE 10V
MRM MEASUREMENT CONDITION 2:
　PRECURSOR ION 4 (m/z 300) > PRODUCT ION (m/z 50), CE 35V Fig. 4A
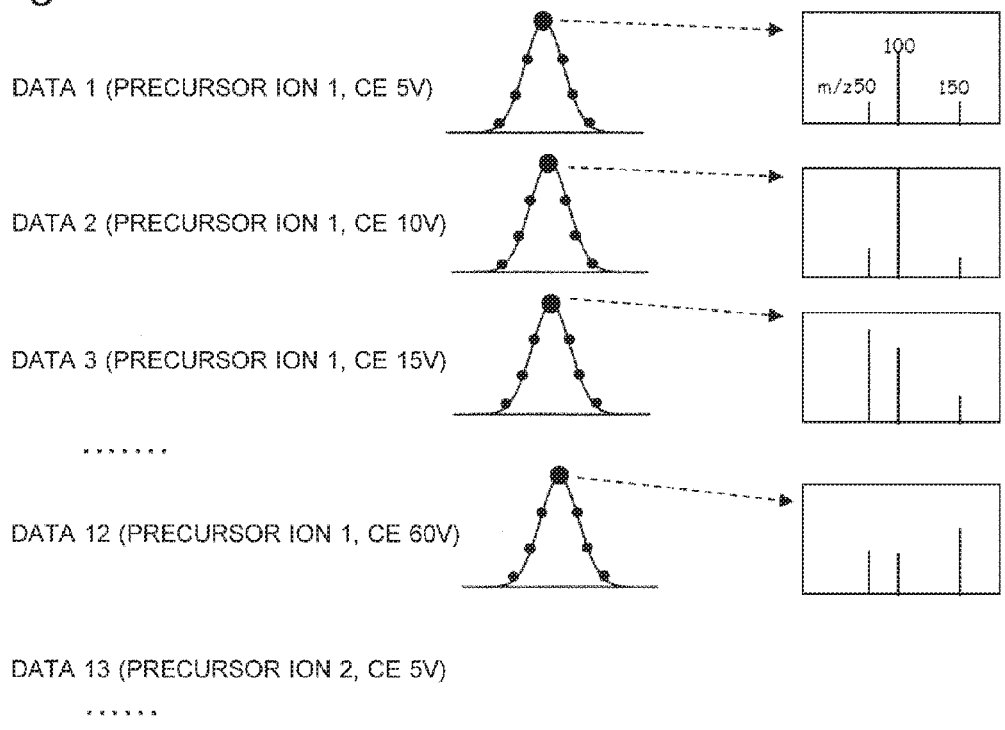
DATA 13 (PRECURSOR ION 2, CE 5V)
.......
DATA 60 (PRECURSOR ION 5, CE 60V)
Fig. 4B
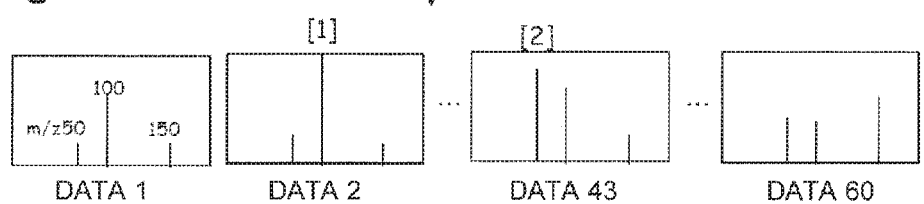
Fig. 4C
MRM MEASUREMENT CONDITION 1:
   PRECURSOR ION 1 (m/z 200) > PRODUCT ION (m/z 100), CE 10V
MRM MEASUREMENT CONDITION 2:
   PRECURSOR ION 4 (m/z 300) > PRODUCT ION (m/z 50), CE 35V

MASS SPECTROMETRY METHOD, CHROMATOGRAPH MASS SPECTROMETER, AND PROGRAM FOR MASS SPECTROMETRY

CROSS REFERENCE TO RELATED APPLICATIONS

This application is a National Stage of International Application No. PCT/JP2015/053113, filed on Feb. 4, 2015, the contents of all of which are incorporated herein by reference in their entirety.

TECHNICAL FIELD

The present invention relates to a mass spectrometry method and program for mass spectrometry for optimizing the condition of a multiple reaction monitoring (MRM) measurement of a target compound contained in a sample.

BACKGROUND ART

As one mass spectrometric technique for qualitative and quantitative determination of a target compound contained in a sample, there is a technique called the "MS/MS analysis (tandem analysis)". For example, the MS/MS analysis is performed using a mass spectrometer having a front mass separator for selecting a precursor ion, a collision cell for fragmenting the precursor ion into product ions, and a rear mass separator for selecting a product ion. One example of such a mass spectrometer is a tandem quadrupole mass spectrometer.

An MRM measurement is one mode of the measurement in the MS/MS analysis. In the MRM measurement, the mass-to-charge ratio of the ions which are allowed to pass through is fixed in each of the front and rear mass spectrometers so as to measure the intensity (amount) of a specific kind of product ion corresponding to a specific kind of precursor ion. Such a combination of the precursor ion and product ion is called the "MRM transition". In the MRM measurement, ion intensity signals can be obtained with high signal-to-noise ratios, since the two-stage mass separators remove ions which originate from compounds which are not the measurement target or from foreign components, as well as neutral particles. Accordingly, the MRM measurement is particularly effective in such analyses as a quantitative determination of a trace amount of a component.

In order to perform an MRM measurement for a target compound, it is necessary to previously determine the MRM measurement condition. The MRM measurement condition includes the MRM transition as well as the value of the collision energy (CE) for inducing the fragmentation of the precursor ion within the collision cell. Since the magnitude of the CE value affects the generation efficiency of the product ions, a combination of the MRM transition and CE value which yields the highest level of detection sensitivity should be set as the MRM measurement condition.

The MRM transition and CE value have conventionally been determined as follows:

Initially, an analysis operator enters one or more precursor-ion candidates to be generated from the target compound and a plurality of CE-value candidates on a control software program for the mass spectrometer. The control software program determines all possible combinations of the entered precursor-ion candidates and CE-value candidates as the measurement conditions. Subsequently, a product-ion scan measurement is performed using one of those measurement conditions. This task is performed under each of all of the measurement conditions, to acquire product-ion spectra (FIG. 4A). From all of the product-ion spectra obtained in this manner (FIG. 4B), product ions are selected in descending order of the detection intensity, and the combination of each selected product ion and corresponding precursor-ion candidate (MRM transition), as well as the CE-value candidate at which the product-ion spectrum concerned was obtained, are determined as the MRM measurement condition (FIG. 4C; for example, see Patent Literature 1 or 2).

Such a product-ion scan measurement is normally performed under the condition that a standard sample which is the target compound in pure form is directly introduced into the mass spectrometer.

CITATION LIST

Patent Literature

Patent Literature 1: JP 2013-15485 A
Patent Literature 2: JP 2012-104389 A

SUMMARY OF INVENTION

Technical Problem

However, for a compound contained in a sample obtained from soil or originating from a living organism, it may be difficult to obtain the target compound in pure form as the standard sample. In such a case, the measurement target sample itself is introduced into a chromatograph mass spectrometer having a chromatograph (gas or liquid chromatograph) and a mass spectrometer, and the product-ion scan measurement is performed in the mass spectrometer after the target compound has been isolated from the other compounds in the chromatograph. In this case, there is only a limited period of time during which the target compound is introduced from the chromatograph into the mass spectrometer, and furthermore, the quantity of the target compound introduced into the mass spectrometer temporally changes within that limited period of time. To solve this problem, in a conventional method, the measurement target sample is introduced into the chromatograph mass spectrometer for each of all combinations of the precursor-ion candidate and CE-value candidate mentioned earlier. Every time the sample is introduced, a product-ion spectrum is acquired within a segment of time around the point in time where the quantity of the target compound introduced from the chromatograph into the mass spectrometer reaches the highest level (the point corresponding to the peak top of the chromatogram), and the MRM measurement condition is determined based on the detection intensities of the product ions in that product-ion spectrum.

However, if a large number of combinations of the precursor-ion candidate and the CE-value candidate are selected in order to optimize the MRM measurement condition, the previous method requires the measurement sequence including the introduction of the measurement target sample into the chromatograph, isolation of the target compound and product-ion scan measurement for the target compound to be performed a large number of times. For example, if there are five precursor ions and twelve CE-value candidates ranging from 5 V to 60 V at intervals of 5 V, the aforementioned measurement sequence needs to be performed 60 times. Performing the measurement such a large number of times requires a considerable length of time for the optimization of the MRM measurement condition. Furthermore, when there is only a trace amount of sample available for the measurement, it is in the first place difficult to set a large number of aforementioned combinations and exhaustively perform the product-ion scan measurement for all of those combinations.

The problem to be solved by the present invention is to provide a mass spectrometry method, chromatograph mass spectrometer, and program for mass spectrometry capable of optimizing the MRM measurement condition for a target compound within a short period of time as well as optimizing the MRM measurement condition even when there is only a trace amount of sample available for the measurement.

Solution to Problem

The first aspect of the present invention developed for solving the previously described problem is a method for optimizing the condition of a multiple reaction monitoring measurement of a target compound contained in a sample using a chromatograph mass spectrometer including a chromatograph and a mass spectrometer having front and rear mass separators with a collision cell in between, the method including:

a) creating a plurality of measurement conditions corresponding to all combinations of one or more precursor-ion candidates generated from the target compound and one or more collision-energy-value candidates;

b) introducing the sample into the chromatograph mass spectrometer;

c) performing a product-ion scan measurement at least one time using each of the plurality of measurement conditions as well as performing, a plurality of times and under the same condition, a reference measurement for detecting a predetermined kind of ion generated from the target compound, within an introduction time during which the target compound isolated by a column in the chromatograph is introduced into the mass spectrometer;

d) creating a peak function, which is a function representing a change in the amount of introduction of the target compound into the mass spectrometer within the introduction time, based on the result of the reference measurement;

e) creating a normalization function for normalizing the amount of introduction of the target compound within the introduction time, based on the peak function; and f) normalizing the intensity of product-ion spectra obtained by the product-ion scan measurements performed for all of the aforementioned combinations, using the normalization function.

The reference measurement is a measurement performed in order to grasp the change in the amount of introduction of the target compound within the introduction time. For example, it may be a selected ion monitoring (SIM) measurement. It is also possible to perform a precursor-ion scan measurement and use the total intensity of the detected ions. The peak function may be, for example, a Gaussian function.

In the mass spectrometry method according to the present invention, within the introduction time during which the target compound is introduced from the column in the chromatograph into the mass spectrometer, the product-ion scan measurement is performed at least one time for each of all combinations of one or more precursor-ion candidates and one or more collision-energy-value candidates, and additionally, the reference measurement for detecting a predetermined kind of ion under the same condition is performed a plurality of times. Based on the result of the reference measurement, a normalization function for normalizing the amount of introduction of the target compound within the introduction time is created, and the intensity of the product-ion spectra obtained for all of the aforementioned combinations are normalized.

In the mass spectrometry method according to the present invention, all product-ion spectra necessary for the optimization of the MRM measurement condition can be acquired by a single execution of the measurement sequence including the introduction of a sample into the chromatograph, isolation of the target compound, and product-ion scan measurement of the target compound. Accordingly, the optimization of the MRM measurement condition can be completed within a short period of time. Furthermore, the MRM measurement condition can be optimized even when there is only a trace amount of sample available for the measurement.

The reference measurement may preferably be performed at least one time within each of the first and second halves of the introduction time. This will even further improve the accuracy of the peak function.

For a product-ion scan measurement performed at a timing when the amount of introduction of the target component was relatively low, the normalization function magnifies the product-ion spectrum in its intensity by a larger factor, so that the measurement error becomes relatively large.

Accordingly, it is preferable to perform the product-ion scan measurement at least two times for each of all of the aforementioned combinations. This will reduce the measurement error of the product-ion spectra.

The second aspect of the present invention developed for solving the previously described problem is a chromatograph mass spectrometer used for optimizing the condition of a multiple reaction monitoring measurement of a target compound contained in a sample, including:

a) a chromatograph having a column for isolating the target compound from the other compounds;

b) a mass spectrometer having front and rear mass separators with a collision cell in between;

c) a measurement condition creator for creating a plurality of measurement conditions corresponding to all combinations of one or more precursor-ion candidates and one or more collision-energy-value candidates, based on a user input;

d) a measurement executor for performing a product-ion scan measurement at least one time under each of the plurality of measurement conditions as well as performing, a plurality of times and under the same condition, a reference measurement for detecting a predetermined kind of ion generated from the target compound, within an introduction time during which the target compound isolated by the column is introduced into the mass spectrometer;

e) a peak function creator for creating a peak function, which is a function representing a change in the amount of introduction of the target compound into the mass spectrometer within the introduction time, based on the result of the reference measurement;

f) a normalization function creator for creating a normalization function for normalizing the amount of introduction of the target compound within the introduction time, based on the peak function; and g) a spectrum intensity normalizer for normalizing the intensity of product-ion spectra obtained by the product-ion scan measurements performed for all of the aforementioned combinations, using the normalization function.

A program for mass spectrometry as the third aspect of the present invention developed for solving the previously described problem is characterized by making a computer function as the measurement condition creator, measurement executor, peak function creator, normalization function creator and spectrum intensity normalizer as described in the second aspect of the preset invention.

Advantageous Effects of the Invention

By using the mass spectrometry method, chromatograph mass spectrometer, or program for mass spectrometry according to the present invention, the MRM measurement condition for a target compound can be optimized within a short period of time. Furthermore, the MRM measurement condition can be optimized even when there is only a trace amount of sample available for the measurement.

BRIEF DESCRIPTION OF DRAWINGS

FIGS. 3A-3C are diagrams illustrating the method of the present embodiment for optimizing the MRM measurement condition.

FIGS. 4A-4C are diagrams illustrating a conventional method for optimizing the MRM measurement condition.

DESCRIPTION OF EMBODIMENTS

Figure 1:
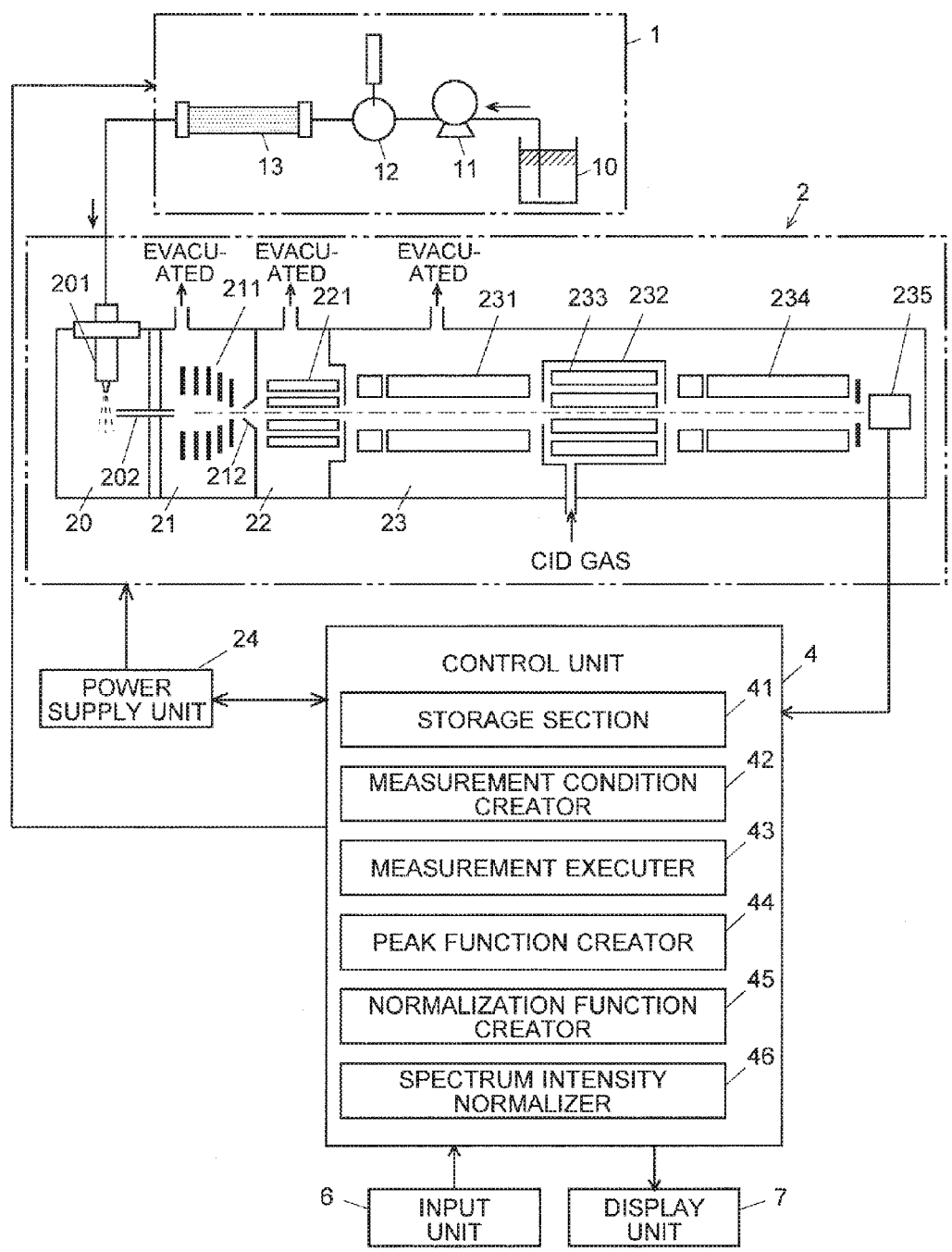
FIG. 1 is a configuration diagram of the main components of a liquid chromatograph mass spectrometer as one embodiment of the chromatograph mass spectrometer according to the present invention.
Figure 2:
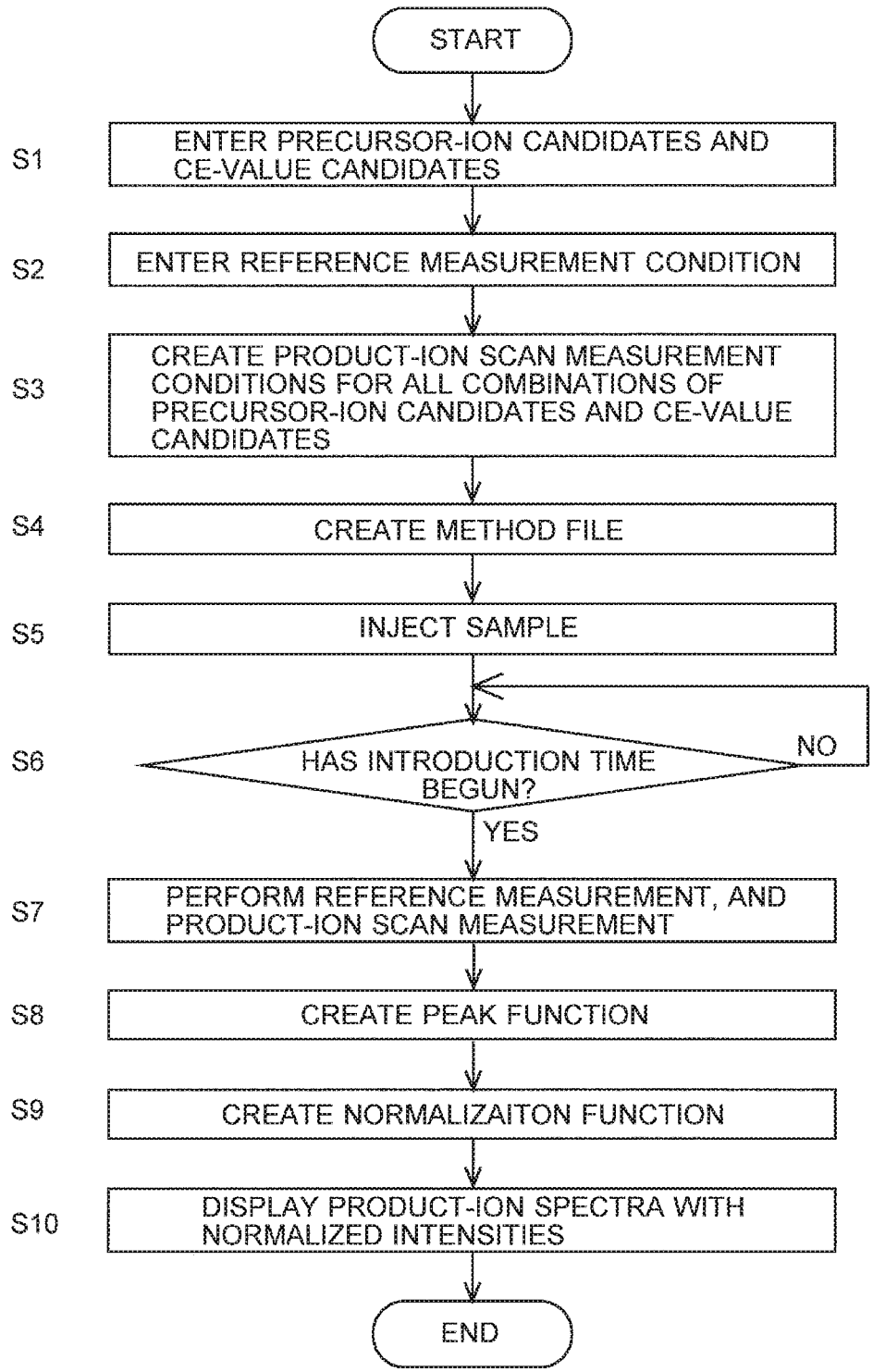
FIG. 2 is a flowchart in one embodiment of the mass spectrometry method according to the present invention.

One embodiment of the mass spectrometry method, chromatograph mass spectrometer and program for mass spectrometry according to the present invention is hereinafter described with reference to the attached drawings. FIG. 1 is a configuration diagram of the main components of a liquid chromatograph mass spectrometer of the present embodiment. FIG. 2 is a flowchart concerning the mass spectrometry method of the present embodiment.

The chromatograph mass spectrometer of the present embodiment is a liquid chromatograph mass spectrometer composed of a liquid chromatograph unit 1, mass spectrometer unit 2, and control unit 4 for controlling the operations of those units.

In the liquid chromatograph mass spectrometer of the first embodiment, the liquid chromatograph unit 1 includes a mobile phase container 10 in which a mobile phase is stored, a pump 11 for drawing the mobile phase and supplying it at a fixed flow rate, an injector 12 for injecting a predetermined amount of sample liquid into the mobile phase, and a column 13 for temporally separating various compounds contained in the sample liquid.

The mass spectrometer unit 2 has the configuration of a multi-stage differential pumping system including an ionization chamber 20 maintained at approximately atmospheric pressure and an analysis chamber 23 evacuated to a high degree of vacuum by a vacuum pump (not shown), between which first and second intermediate vacuum chambers 21 and 22 are provided having their degrees of vacuum increased in a stepwise manner. The ionization chamber 20 is provided with an electrospray ionization probe (ESI probe) 201 for spraying a sample solution while imparting electric charges to the same solution. The ionization chamber 20 communicates with the first intermediate vacuum chamber 21 in the next stage via a thin heated capillary 202. The first intermediate vacuum chamber 21 is separated from the second intermediate vacuum chamber 22 by a skimmer 212 having a small hole at its apex. The first and second intermediate vacuum chambers 21 and 22 respectively contain ion guides 211 and 221 for transporting ions to the next stage while converging the ions. The analysis chamber 23 contains a front quadrupole mass filter (Q1) 231 which separates ions according to their mass-to-charge ratios and a rear quadrupole mass filter (Q3) 234 which also separates ions according to their mass-to-charge ratios, with a collision cell 232 containing a multipole ion guide (q2) 233 placed between the two mass filters, as well as an ion detector 235.

A CID gas, such as argon or nitrogen, can be continuously or intermittently supplied into the collision cell 232. A power supply unit 24 applies predetermined voltages to the ESI probe 201, ion guides 211, 221 and 233, quadrupole mass filters 231 and 234 as well as other elements, respectively. In each of the quadrupole mass filters 231 and 234, pre-rod electrodes for correcting the disturbance of the electric field at the inlet end are provided before the main rod electrodes. A voltage which is different from those applied to the main rod electrodes can be applied to the pre-rod electrodes.

The mass spectrometer unit 2 can perform various measurements, such as a selected ion monitoring (SIM) measurement, product-ion scan measurement, and multiple reaction monitoring (MRM) measurement. In the SIM measurement, no selection of an ion is performed in the front quadrupole mass filter (Q1) 231 (i.e. this mass filter is disabled from functioning), while the rear quadrupole mass filter (Q3) 234 is operated to allow ions to pass through this filter only at a fixed mass-to-charge ratio and be detected.

On the other hand, in the MS/MS scan measurement (product ion scan measurement) and MRM measurement, the front quadrupole mass filter (Q1) 231 and rear quadrupole mass filter (Q3) 234 are both made to function as the mass filters. The front quadrupole mass filter (Q1) 231 allows only an ion designated as the precursor ion to pass through. Additionally, the CID gas is supplied into the collision cell 232 so as to fragment the precursor ion into product ions. In the MS/MS scan measurement, the mass-to-charge ratio of the ion to be allowed to pass through the rear quadrupole mass filter (Q3) 234 is continuously changed. In the MRM measurement, the mass-to-charge ratio of the ion to be allowed to pass through the rear quadrupole mass filter (Q3) 234 is fixed.

The control unit 4 has a storage section 41 and the following functional blocks: a measurement condition creator 42, measurement executor 43, peak function creator 44, normalization function creator 45 and spectrum intensity normalizer 46. The same unit also has the function of controlling the operations of the relevant elements, such as the pump 11 and injector 12 in the liquid chromatograph unit 1 as well as the power supply unit 24 and CID gas supplier (not shown) in the mass spectrometer unit 2, in accordance with the operations of those functional blocks. The control unit 4 is actually a personal computer, which can fulfil the functions as the control unit 4 by executing a program for mass spectrometry (which corresponds to the mass spectrometry program in the present embodiment) previously installed on this computer. The control unit 4 has an input unit 6 and display unit 7 connected to it.

The mass spectrometry method in the present embodiment is hereinafter described with reference to the flowchart of FIG. 2. The present embodiment deals with the case of optimizing the condition of an MRM measurement of a target compound contained in a sample.

Initially, an analysis operator enters, through the input unit 6, the period of time (peak beginning time and peak ending time on the chromatogram) within which the target compound contained in the sample is introduced from the column 13 in the liquid chromatograph unit 1 into the mass spectrometer unit 2. The analysis operator also enters the precursor-ion candidates (in the present embodiment, five kinds of precursor-ion candidates) and CE-value candidates (in the present embodiment, 12 candidates ranging from 5 V to 60 V at intervals of 5 V) as well as the number of times of the product-ion scan measurement (in the present embodiment, two times; Step S1). Additionally, the analysis operator enters the condition of a reference measurement which will be described later (in the present embodiment, an SIM measurement of one of the precursor-ion candidates) and the number of times of the reference measurement (in the present embodiment, three times; Step S2).

After the measurement conditions and numbers of times of the measurements have been entered by the analysis operator, the measurement condition creator 42 stores them in the storage section 41 as well as creates a product-ion scan measurement condition for each of all of the combinations of the precursor-ion candidates and CE-value candidates (in the present embodiment, 60 combinations; Step S3). Subsequently, the measurement executor 43 creates a method file for performing the reference measurement (one time), product-ion scan measurements (60 combinations×1 time), reference measurement (one time), product-ion scan measurement (60 combinations×1 time) and reference measurement (one time) in the mentioned order, and stores this file in the storage section 41 (Step S4).

The reference measurement is performed at the peak beginning time, peak top time and peak ending time, one measurement each time. The product-ion scan measurement is performed within the period of time between one reference measurement and the next. The execution times of the reference measurement and the product-ion scan measurement (including the period of time necessary for changing the voltages applied to the relevant sections in the mass spectrometer unit 2) are determined based on the length of the introduction time for the target compound and the number of times of the measurement. In this manner, a method file for executing the measurements as shown in FIG. 3A is created.

When a command to initiate the measurement is issued by a predetermined operation by the analysis operator, the measurement executor 43 introduces a predetermined amount of measurement target sample from the injector 12 in the liquid chromatograph unit 1. Then, it stands by until the beginning of the period of time during which the target compound contained in the sample is introduced from the column 13 into the ESI probe 201 in the mass spectrometer unit 2 (introduction time; Step S6). When the introduction time for the target compound is reached ("YES" in Step S6), the measurement executor 43 performs the reference measurement (three times) and product-ion scan measurement (60 combinations×2 times) based on the aforementioned method file, and stores the measured data in the storage section 41 (Step S7).

After those measurements have been completed, the peak function creator 44 reads the reference measurement data of the three points from the storage section 41 and creates a peak function (Step S8). In the present embodiment, the peak function is created by fitting a Gaussian function to the three points of reference measurement data and stored in the storage section 41. This peak function represents the change in the amount of the target compound supplied to the mass spectrometer unit 2 within the introduction time for the target compound.

Subsequently, the normalization function creator 45 creates a normalization function, which is the inverse function of the peak function, and stores it in the storage section 41 (Step S9). This normalization function will be used to normalize the amount of introduction of the target compound which changes within the introduction time.

After the normalization function has been created, the spectrum intensity normalizer 46 reads the product-ion scan measurement data from the storage section 41 and normalizes the intensities of the ions detected in each measurement, using the normalization function. Subsequently, it averages the measurement data acquired two times for each combination of the precursor-ion candidate and the CE-value candidate, to create a product-ion spectrum corresponding to each combination and display it on the display unit 7 (Step S10) (FIG. 3B). Along with the product-ion spectra, the corresponding precursor-ion candidates and CE-value candidates as well as the mass-to-charge ratios of the detected product ions are also listed in descending order of the detection intensity of the product ions on the display unit 7. The analysis operator extracts the required number of combinations from the list shown on the display unit 7 and determines the MRM measurement conditions (MRM transition and CE value; FIG. 3C).

As described thus far, with the chromatograph mass spectrometer, mass spectrometry method and program for mass spectrometry of the present embodiment, the reference measurements (three times) and product-ion scan measurements for all combinations of the precursor-ion candidates and CE-value candidates (two times for each combination) can be executed in a single measurement process, and product-ion spectra for all combinations can be obtained. Additionally, the normalization function for normalizing the change in the amount of introduction of the target compound within the introduction time is created based on the reference measurement data, and the intensity of the product-ion spectra is normalized using this function. Therefore, the product-ion spectra for all combinations can be obtained with accurate intensities by a single measurement process. Accordingly, the MRM measurement condition for the target compound can be optimized within a short period of time. Furthermore, the MRM measurement condition can be optimized even when there is only a trace amount of sample available for the measurement.

The previous embodiment is a mere example and can be appropriately changed in accordance with the gist of the present invention.

Although the previously described embodiment is concerned with the case of optimizing the MRM measurement condition using a liquid chromatograph mass spectrometer, the MRM measurement condition in a gas chromatograph mass spectrometer can also be similarly optimized.

As opposed to the previous embodiment in which a Gaussian function is used as the peak function, a different type of function or polynomial may also be used to create the peak function.

In the previous embodiment, the reference measurement is performed three times. If the position (time) of the peak top in the chromatogram of the target compound is previously known, the peak function can be created by performing the reference measurement at least two times. Needless to say, the reference measurement may be performed four or more times to improve the accuracy of the peak function. In the previous embodiment, an SIM measurement is performed as the reference measurement and the detection intensity of an ion is used as the reference measurement data. It is also possible to perform an MS scan measurement as the reference measurement and use the total intensity of ions as the reference measurement data, or to perform an MRM measurement for a specific MRM transition as the reference measurement and use the detection intensity of a product ion as the reference measurement data. If there are preliminary measurement data of the target compound obtained to determine precursor-ion candidates, it is possible to create the peak function and normalization function from those preliminary measurement data instead of performing the reference measurement to create the peak function.

In the previous embodiment, the product-ion scan measurement is performed two times for each combination. This number of times may also be appropriately changed. However, it should be noted that, for a product-ion scan measurement performed at a timing when the amount of introduction of the target component was relatively low, the normalization function magnifies the product-ion spectrum in its intensity by a larger factor, so that the measurement error becomes relatively large. Therefore, it is preferable to perform the measurement at least two times for each combination. This reduces the magnitude of the measurement error in the product-ion spectrum. Increasing the number of times of the product-ion measurement reduces the variation of the measurement depending on the change in the amount of introduction of the target compound. However it also reduces the period of time for each measurement, causing measurement errors to occur more easily. Accordingly, analysis operators should determine the number of times of the measurement in each case, taking into account the length of the introduction time and the number of times of the measurement.

REFERENCE SIGNS LIST

1 . . . Liquid Chromatograph
10 . . . Mobile Phase Container
11 . . . Pump
12 . . . Injector
13 . . . Column
2 . . . Mass Spectrometer Unit
20 . . . Ionization Chamber
201 . . . ESI Probe
202 . . . Heated Capillary
21 . . . First Intermediate Vacuum Chamber
211 . . . Ion Guide
212 . . . Skimmer
22 . . . Second Intermediate Vacuum Chamber
23 . . . Analysis Chamber
231 . . . Quadrupole Mass Filter
232 . . . Collision Cell
235 . . . Ion Detector
24 . . . Power Supply Unit
4 . . . Control Unit
41 . . . Storage Section
42 . . . Measurement Condition Creator
43 . . . Measurement Executor
44 . . . Peak Function Creator
45 . . . Normalization Function Creator
46 . . . Spectrum Intensity Normalizer
6 . . . Input Unit
7 . . . Display Unit

The invention claimed is:

1. A mass spectrometry method for optimizing a condition of a multiple reaction monitoring measurement of a target compound contained in a sample using a chromatograph mass spectrometer including a chromatograph and a mass spectrometer having front and rear mass separators with a collision cell in between, the method comprising:
   a) creating a plurality of measurement conditions corresponding to all combinations of one or more precursor-ion candidates generated from the target compound and one or more collision-energy-value candidates;
   b) introducing the sample into the chromatograph mass spectrometer;
   c) performing a product-ion scan measurement at least one time using each of the plurality of measurement conditions as well as performing, a plurality of times and under a same condition, a reference measurement for detecting a predetermined kind of ion generated from the target compound, within an introduction time during which the target compound isolated by a column in the chromatograph is introduced into the mass spectrometer;
   d) creating a peak function, which is a function representing a change in an amount of introduction of the target compound into the mass spectrometer within the introduction time, based on a result of the reference measurement;
   e) creating a normalization function for normalizing the amount of introduction of the target compound within the introduction time, based on the peak function; and
   f) normalizing an intensity of product-ion spectra obtained by the product-ion scan measurements performed for all of the aforementioned combinations, using the normalization function.

2. The mass spectrometry method according to claim 1, wherein the reference measurement is a selected ion monitoring measurement.

3. The mass spectrometry method according to claim 2, wherein the reference measurement is performed at least one time within each of first and second halves of the introduction time.

4. The mass spectrometry method according to claim 3, wherein the product-ion scan measurement is performed at least two times for each of all of the aforementioned combinations within the introduction time.

5. The mass spectrometry method according to claim 2, wherein the product-ion scan measurement is performed at least two times for each of all of the aforementioned combinations within the introduction time.

6. The mass spectrometry method according to claim 1, wherein the reference measurement is performed at least one time within each of first and second halves of the introduction time.

7. The mass spectrometry method according to claim 6, wherein the product-ion scan measurement is performed at least two times for each of all of the aforementioned combinations within the introduction time.

8. The mass spectrometry method according to claim 1, wherein the product-ion scan measurement is performed at least two times for each of all of the aforementioned combinations within the introduction time.

9. A chromatograph mass spectrometer used for optimizing a condition of a multiple reaction monitoring measurement of a target compound contained in a sample, comprising:
   a) a chromatograph having a column for isolating the target compound from other compounds;

b) a mass spectrometer having front and rear mass separators with a collision cell in between;

c) a measurement condition creator for creating a plurality of measurement conditions corresponding to all combinations of one or more precursor-ion candidates and one or more collision-energy-value candidates, based on a user input;

d) a measurement executor for performing a product-ion scan measurement at least one time under each of the plurality of measurement conditions as well as performing, a plurality of times and under a same condition, a reference measurement for detecting a predetermined kind of ion generated from the target compound, within an introduction time during which the target compound isolated by the column is introduced into the mass spectrometer;

e) a peak function creator for creating a peak function, which is a function representing a change in an amount of introduction of the target compound into the mass spectrometer within the introduction time, based on a result of the reference measurement;

f) a normalization function creator for creating a normalization function for normalizing the amount of introduction of the target compound within the introduction time, based on the peak function; and g) a spectrum intensity normalizer for normalizing an intensity of product-ion spectra obtained by the product-ion scan measurements performed for all of the aforementioned combinations, using the normalization function.

10. A non-transitory computer readable medium recording a program for mass spectrometry used for optimizing a condition of a multiple reaction monitoring measurement of a target compound contained in a sample using a chromatograph mass spectrometer including a chromatograph and a mass spectrometer having front and rear mass separators with a collision cell in between, the program characterized by making a computer function as:

a) a measurement condition creator for creating a plurality of measurement conditions corresponding to all combinations of one or more precursor-ion candidates and one or more collision-energy-value candidates, based on a user input;

b) a measurement executor for performing a product-ion scan measurement at least one time under each of the plurality of measurement conditions as well as performing, a plurality of times, a reference measurement for detecting a predetermined kind of ion generated from the target compound under a same condition, within an introduction time during which the target compound isolated by the column is introduced into the mass spectrometer;

c) a peak function creator for creating a peak function, which is a function representing a change in an amount of introduction of the target compound into the mass spectrometer within the introduction time, based on a result of the reference measurement;

d) a normalization function creator for creating a normalization function for normalizing the amount of introduction of the target compound within the introduction time, based on the peak function; and e) a spectrum intensity normalizer for normalizing an intensity of product-ion spectra obtained by the product-ion scan measurements performed for all of the aforementioned combinations, using the normalization function.

\* \* \* \* \*